United States Patent
Fletcher

(10) Patent No.: US 11,517,025 B2
(45) Date of Patent: *Dec. 6, 2022

(54) SPECIALITY LOW SATURATES CANOLA OIL

(71) Applicant: CARGILL, INCORPORATED, Wayzata, MN (US)

(72) Inventor: Richard Fletcher, Windsor, CO (US)

(73) Assignee: Cargill, Incorporated, Wayzata, MN (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/323,622

(22) PCT Filed: Aug. 1, 2017

(86) PCT No.: PCT/US2017/044874
§ 371 (c)(1),
(2) Date: Feb. 6, 2019

(87) PCT Pub. No.: WO2018/031293
PCT Pub. Date: Feb. 15, 2018

(65) Prior Publication Data
US 2019/0174788 A1 Jun. 13, 2019

Related U.S. Application Data

(60) Provisional application No. 62/374,244, filed on Aug. 12, 2016.

(51) Int. Cl.
| | |
|---|---|
| A23D 9/02 | (2006.01) |
| A23L 33/12 | (2016.01) |
| A01H 6/20 | (2018.01) |
| C11B 1/00 | (2006.01) |
| A23D 9/00 | (2006.01) |
| A01H 5/10 | (2018.01) |

(52) U.S. Cl.
CPC ............ *A23D 9/02* (2013.01); *A01H 5/10* (2013.01); *A01H 6/202* (2018.05); *A23D 9/00* (2013.01); *A23L 33/12* (2016.08); *C11B 1/00* (2013.01); *A23V 2002/00* (2013.01); *A23V 2200/326* (2013.01); *A23V 2200/3262* (2013.01); *A23V 2250/1872* (2013.01); *A23V 2250/1874* (2013.01); *A23V 2300/31* (2013.01)

(58) Field of Classification Search
None
See application file for complete search history.

(56) References Cited

U.S. PATENT DOCUMENTS

| | | |
|---|---|---|
| 4,948,811 A | 8/1990 | Lin et al. |
| 5,387,758 A | 2/1995 | Wong et al. |
| 5,434,283 A | 7/1995 | Wong et al. |
| 5,545,821 A | 8/1996 | Wong et al. |
| 5,638,637 A | 6/1997 | Wong et al. |
| 5,840,946 A | 11/1998 | Wong |
| 5,861,187 A | 1/1999 | Debonte et al. |
| 5,952,544 A | 9/1999 | Browse et al. |
| 5,965,755 A | 10/1999 | Sernyk et al. |
| 6,051,539 A | 4/2000 | Kodali et al. |
| 6,063,947 A | 5/2000 | Debonte et al. |
| 6,169,190 B1 | 1/2001 | Lanuza et al. |
| 6,291,409 B1 | 9/2001 | Kodali et al. |
| 6,303,849 B1 * | 10/2001 | Potts ............... A01H 5/10 800/260 |
| 6,407,317 B2 | 6/2002 | Fan |
| 6,787,686 B2 * | 9/2004 | Potts ............... A01H 5/10 800/306 |
| 8,981,180 B2 | 3/2015 | Laga et al. |
| 9,334,483 B2 * | 5/2016 | Zheng ............ C12N 15/8247 |
| 9,920,303 B2 | 3/2018 | Laga et al. |
| 10,709,079 B2 * | 7/2020 | Zheng ............ A01H 1/00 |
| 2005/0039233 A1 * | 2/2005 | Yao ............... C12N 9/0083 800/281 |
| 2008/0168587 A1 * | 7/2008 | Yao ............... C12N 15/8247 800/306 |
| 2008/0199587 A1 | 8/2008 | Debonte et al. |
| 2010/0143570 A1 * | 6/2010 | Ripley ............. A01H 5/10 426/629 |
| 2012/0216319 A1 | 8/2012 | Coonrod et al. |
| 2012/0246755 A1 | 9/2012 | Laga et al. |
| 2013/0031678 A1 * | 1/2013 | Zheng ............ C12N 15/8247 800/306 |
| 2015/0232951 A1 | 8/2015 | Laga et al. |
| 2015/0334976 A1 | 11/2015 | Chungu et al. |
| 2016/0208195 A1 * | 7/2016 | Zheng ............ C12Q 1/6895 |

FOREIGN PATENT DOCUMENTS

| | | |
|---|---|---|
| WO | 9108676 W | 6/1991 |
| WO | 9306714 A1 | 4/1993 |
| WO | 9950430 A2 | 10/1999 |
| WO | 2011075716 A1 | 6/2011 |
| WO | 2011150028 A2 | 12/2011 |
| WO | 2015077661 A1 | 5/2015 |
| WO | 2018031293 A1 | 2/2018 |

OTHER PUBLICATIONS

Scarth R. et al., Designer Oil Canola—a review of new food-grade brassica oils with focus on high oleic, low linolenic types, Proceedings International Rapeseed Congress, No. 10th, Jan. 1, 1999 (Jan. 1,199) pp. 1-7, XP002513934, p. 4, paragraph 2.

* cited by examiner

*Primary Examiner* — Patricia A George

(57) ABSTRACT

Specialty canola oil is provided with preferred stability, flavor, and low levels of saturates. Plants, seeds, and oil contain 3.5% to 5% total saturates, greater than 18% linoleic acid, and less than 3% linolenic acid. The oil of the invention provides not only lower saturates levels but also acceptable frying stability and improved flavor.

11 Claims, No Drawings

SPECIALITY LOW SATURATES CANOLA OIL

CROSS-REFERENCE TO RELATED APPLICATIONS

This application is a national phase application of international application PCT/US 2017/044874, filed Aug. 1, 2017, entitled SPECIALITY LOW SATURATES CANOLA OIL, which application claims the benefit of U.S. Provisional Patent Application Ser. No. 62/374,244, filed on Aug. 12, 2016, entitled SPECIALITY LOW SATURATES CANOLA OIL, which application is hereby incorporated by reference herein in its entirety.

BACKGROUND

The invention generally relates to canola oils containing low levels of saturated fatty acids. Diets high in saturated fatty acids, or saturates, have been linked to higher levels of cholesterol and an increased risk of cardiovascular disease. Current dietary guidelines recommend that saturated fat intake should not be more than 10% of total calories. Therefore based on a 2,000 calorie a day diet, no more than about 20 grams of saturated fat should be consumed per day. To increase consumer awareness of this recommendation the FDA's labeling guidelines require that any food carrying the "low sat" label contain less than 1 gram of saturated fat per 14 gram serving. Any food labeled as "no sat" must contain less than 0.5 grams of saturated fat per 14 gram serving. In addition to the desire for reduced levels of saturated fats, oils used in food applications including frying must exhibit other important characteristics such as stability, cost acceptability, and a desirable flavor profile. The present invention provides novel canola oils with a combination of stability, flavor, and low total saturates.

SUMMARY

Canola oils of the present invention are particularly useful for frying applications. The major challenges faced by fast food restaurants in frying involves the desire to have a good tasting oil that is also stable to the intense high heat and moisture inherent in frying conditions. Coupled with those challenges is the desire to have oils that are also reduced in saturated fatty acids. Fully saturated fats, either naturally occurring or produced through hydrogenation of other oils have excellent stability, however, these oils are viewed negatively by the public. The oils of the present invention were developed to address the three pronged need for a frying oil to be stable, great tasting, and low in total saturates. Stability is achieved by maintaining a low content of linolenic acid (C18:3). This fatty acid is particularly susceptible to oxidation in the frying environment. Flavor is maintained by keeping a high content of linoleic acid (C18:2). Finally, the customer awareness around saturated fat is managed by having an oil with less than 5% total saturates. All three of these important parameters had never been achieved in canola crop. Accordingly, oils of the present invention can be used produce fried foods such as snack chips (e.g., corn or potato chips), french fries, or other quick serve foods.

The present invention relates to canola plants, seeds, and oils that contain low levels of saturated fatty acids but also have an enhanced flavor profile and good frying stability. The canola plants, seeds, oil, and methods of production are described below.

A canola plant comprising seed wherein the seed comprises an oil and wherein the oil has:
a) a total saturates content of 3.5% to 5%;
b) a linoleic acid content of greater than 18%; and
c) a linolenic acid content of less than 3.0%.

A food composition comprising an edible canola oil wherein the oil comprises:
a) a total saturates content of from 3.5% to 5%;
b) a linoleic acid content of greater than 18%; and
c) a linolenic acid content of less than 3.0%.

A canola oil comprising:
a) a total saturates content of from 3.5% to 5%;
b) a linoleic acid content of greater than 18%; and
c) a linolenic acid content of less than 3.0%.

A method of producing a canola oil comprising the steps of:
a) crushing a canola seed to yield a crude oil wherein the crude oil comprises:
i) a total saturates content of 3.5% to 5%;
ii) an linoleic acid content of greater than 18%; and
iii) an linolenic acid content of less than 3.0%; and
b) refining the crude oil to yield a refined canola oil.

DETAILED DESCRIPTION

The canola oil of the present invention is defined by a novel combination of features that leads to improved performance as a frying oil.

"Total Saturates", as used herein, means the combination of the percentages of the following fatty acids which may be present in canola oils. Total Saturates refers to the total of myristic acid (C14:0), palmitic acid (C16:0), stearic acid (C18:0), arachidic acid (C20:0), behenic acid (C22:0), and lignoceric acid (C24:0).

"Oleic acid", as used herein, means a C18:1 fatty acid.

"Linoleic acid", as used herein, means a C18:2 fatty acid.

"Linolenic acid", as used herein, means a C18:3 fatty acid.

"Non-transgenic", as used herein, means that the canola plants, or canola seeds, do not contain any non-native *Brassica* DNA other than herbicide tolerant traits. The seeds or plants of the present invention may contain transgenic events related to conveyance of herbicide tolerance such as resistance to glyphosate or other herbicides.

"Blended", as used herein, means oils with materially different fatty acid compositions blended together to create a mixture. Including individual canola oils or mixtures of one or more of the following blended together: canola, soy, corn, palm, peanut, coconut, cocoa, flaxseed, sunflower, olive, and the like.

"Refining or refined", as used herein, means crude pressed or extracted canola oils that are treated by chemical or physical means to remove impurities or improve quality. Refining is well known the art and may include one or more steps to remove impurities. Any known processes to remove impurities or improve quality of vegetable oils is included within the definition of refining. See, e.g., *Bailey's Industrial Oil and Fat Products*, (6th Edition, 2005).

"Canola", as used herein means plants from the *Brassica* sp. including: *Brassica juncea, Brassica rapa*, and *Brassica napus*. Reference to a canola "plant" or "plants" includes the plant and its progeny, such as its $F_1$, $F_2$, $F_3$, $F_4$, and subsequent generation plants. In a specific embodiment canola is *Brassica napus*.

"Canola seed" or "seed", as used herein, means the combined seeds harvested from one or more *Brassica* sp. plants.

The fatty acid composition of oil obtained from seed of *Brassica* plants can be determined by methods well known in the art. Typically it can be determined by first crushing and extracting oil from seed samples (e.g., bulk seed samples of 10 or more seeds). TAGs in the seed are hydrolyzed to produce free fatty acids, which then can be converted to fatty acid methyl esters and analyzed using techniques known to the skilled artisan, e.g., gas-liquid chromatography (GLC) according to AOCS Procedure Ce 1-62. Near infrared (NIR) analysis can be performed on whole seed according to AOCS Procedure Am-192 (revised 1999). Numerical values presented herein and in the examples below are a weight percentage. The percentage of a particular fatty acid is described as a percentage of the total fatty acids in the sample as identified empirically. The following fatty acids were measured as part of the evaluation. (C16:0, C16:1, C18:0, C18:1, C18:2, C18:3, C20:0, C20:1, C20:2, C22:0, C22:1, C24:0, and C24:1.)

Seeds harvested from plants described herein can be used to make a crude canola oil or a refined, bleached, and deodorized (RBD) canola oil with a low total saturates content. Harvested canola seed can be crushed by techniques known in the art. The seed can be tempered by spraying the seed with water to raise the moisture to, for example, about 8.5%. The tempered seed can be flaked using a smooth roller with, for example, a gap setting of 0.23 to 0.27 mm. Heat may be applied to the flakes to deactivate enzymes, facilitate further cell rupturing, coalesce the oil droplets, or agglomerate protein particles in order to ease the extraction process. Typically, oil is removed from the heated canola flakes by a screw press to press out a major fraction of the oil from the flakes. The resulting press cake contains some residual oil. Alternatively, the tempered flakes can be extracted with hexane to yield an oil rich miscella. The miscella is subsequently desolventized to yield a crude oil. Both pressed and/or extraction processes are included in the definition of crushing.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles. Canola press cake produced from the screw pressing operation can also be extracted with commercial hexane. The canola oil recovered after solvent evaporation from the extraction process is combined with the clarified oil from the screw pressing operation, resulting in a combined crude oil.

Free fatty acids and gums typically are removed from the crude oil by adding food grade phosphoric acid and heating the acidified oil in a batch refining tank. The acid serves to convert the non-hydratable phosphatides to a hydratable form, and to chelate minor metals that are present in the crude oil. The oil-acid mixture is subsequently treated with sodium hydroxide solution to neutralize the free fatty acids and the remaining phosphoric acid in the acid-oil mixture. The neutralized free fatty acids, metal salts, phosphatides, etc. (soapstock) are drained off from the neutralized oil, A water wash may be done to further reduce the soap content of the oil. The oil may be bleached and deodorized before use, if desired, by standard techniques known in the art. See, e.g., *Bailey's Industrial Oil and Fat Products*, (6th Edition, 2005).

Oils obtained from the *Brassica* plant described herein can have increased oxidative stability, which can be measured using, for example, an Oxidative Stability Index Instrument (e.g., from Omnion, Inc., Rockland, Mass.) according to AOCS Official Method Cd 12b-92 (revised 1993). Oxidative stability is often expressed in terms of "AOM" hours.

Food Compositions

The present disclosure also includes and provides for other food compositions containing the oils described above. For example, oils having a low (less than 5%) total saturated fatty acid content in combination with low linolenic content and high linoleic content can be used to replace or reduce the amount of saturated fatty acids and hydrogenated oils in various food products such that the levels of saturated fatty acids and trans fatty acids are reduced in the food products. In particular, canola oils of the present invention can be used to replace or reduce the amount of saturated fats and hydrogenated oils in processed or packaged food products, including bakery products such as cookies, muffins, doughnuts, pastries (e.g., toaster pastries), pie fillings, pie crusts, pizza crusts, frostings, breads, biscuits, cakes, breakfast cereals, breakfast bars, puddings, and crackers.

For example, an oil described herein can be used to produce sandwich cookies that contain reduced saturated fatty acids and no or reduced levels of hydrogenated oils in the cookie and/or crème filling. In addition to canola oil, such a cookie composition can include, for example, flour, sweetener (e.g., sugar, molasses, honey, high fructose corn syrup, naturally sweet compounds such as those from *Stevia rebaudiana* plants (stevioside, rebaudioside A, B, C, D, and/or E), artificial sweetener such as sucralose, saccharine, aspartame, or acesulfame potassium, and combinations thereof), eggs, salt, flavorants (e.g., chocolate, vanilla, or lemon), a leavening agent (e.g., sodium bicarbonate or other baking acid such as monocalcium phosphate monohydrate, sodium aluminum sulfate, sodium acid pyrophosphate, sodium aluminum phosphate, dicalcium phosphate, glucano-deltalactone, or potassium hydrogen tartrate, or combinations thereof), and optionally, an emulsifier (e.g., mono- and diglycerides of fatty acids, propylene glycol mono- and di-esters of fatty acids, glycerol-lactose esters of fatty acids, ethoxylated or succinylated mono- and diglycerides, lecithin, diacetyl tartaric acid esters or mono- and diglycerides, sucrose esters of glycerol, and combinations thereof). In addition to canola oil, a crème filling composition can include sweetener (e.g., powdered sugar, granulated sugar, honey, high fructose corn syrup, artificial sweetener, or combinations thereof), flavorant (e.g., vanilla, chocolate, or lemon), salt, and, optionally, emulsifier.

Oils described herein also can be used to formulate spray coatings for food products (e.g., cereals or snacks such as crackers). In some embodiments, the spray coating can include other vegetable oils such as sunflower, cottonseed, corn, or soybean oils. A spray coating also can include an antioxidant and/or a seasoning.

Oils described herein also can be used in the manufacturing of dressings, mayonnaises, and sauces to provide a reduction in the total saturated fat content of the product. The low saturate oil can be used as a base oil for creating structured fat solutions such as microwave popcorn solid fats or canola butter formulations.

Linolenic Acid—As mentioned above, to maintain stability C18:3 levels should be kept as low as possible appreciating that it is increasingly difficult to produce plants with ultra low levels of linolenic acid. Embodiments of the present invention have linolenic acid level in canola seed of between 1.5% and 3%. Additional embodiments have levels from i) 1.5% to 2.5%; ii) 1.65% to 2.5%; or iii) 1.1% to 3.1%.

Linoleic—A specific level of C18:2 linoleic acid is desired in the canola seed an oil of the present invention. Embodiments of the present invention have linolenic acid level in the canola seed or oil of greater than 18% or 20%. Additional embodiments have levels from i) 21% to 28%; ii) 24% to 26%; iii) 21.1% to 28.8%; or iv) 18% to 30.6%.

Oleic—Embodiments of the present invention have oleic acid level in the canola seed or oil of greater than 60% or 65%. Additional embodiments have levels from i) 60% to 70%; ii) 63% to 68%; or iii) 59.9% to 73.6%.

Total Saturates—Embodiments of the present invention have a total saturates level of less than 5%. Commodity canola oils commonly used in industry and by consumers have a saturate levels of between 6-8%. See, e.g., *Bailey's Industrial Oil and Fat Products*, Section 2.2, "Canola Oil" on pages 61-121 of Volume 2 (6th Edition, 2005). Embodiments of the present invention have total saturates level in the canola seed or oil of between 3.5% and 5%. Additional embodiments have levels from i) 4% to 5%; ii) 4 to 4.5%; iii) 4.2% to 4.7%; and iv) 3.8% to 5.9%.

All possible combinations of the values for linoleic, linolenic, and total saturates mentioned above are within the scope of the present invention and are specifically contemplated by the inventor. For example, combinations include but are not envisioned to be limited to the following.

TABLE I

| Embodiment | % Linoleic | % Linolenic | % Total Saturates |
|---|---|---|---|
| A | >18 | 1.5-3 | 3.5-5 |
| B | >20 | 1.5-3 | 3.5-5 |
| C | >20 | 1.5-2.75 | 4-5 |
| E | 20-25 | 1.5-2.75 | 3.5-5 |
| F | 21-28 | 1.5-2.75 | 4-5 |
| G | 21-28 | 1.5-2.75 | 4.2-4.7 |
| H | 18-30.6 | 1.1-2.9 | 4.1-5.3 |

Embodiments in Table I can further comprise specific oleic acid content. Examples of embodiments with specific oleic content include hut are not limited to the following: (>60%, >65%, 65% to 70%, 64% to 68%; and 59.9% to 73.6%.)

Further embodiments of the present invention are canola plants, seeds, and oils that are non-transgenic.

Further embodiments of the present invention are canola oils that are not blended or are extracted from a single hybrid variety.

Embodiments of the present invention also include methods of frying food products comprising heating an oil as described herein and immersing a food product in the heated oil. An additional embodiment is the use of the oils described herein for frying foods.

All ranges described in this application and corresponding claims specifically include the designated endpoints as values included in the range.

The invention throughout this disclosure will be further described in the following examples, which do not limit the scope of the invention described in the claims.

EXAMPLES

Examples 1-3

Three examples of plants of the present invention were deposited with the American Type Culture Collection.

| Example | Internal Designation | ATCC Designation |
|---|---|---|
| 1 | 15RH0611 | PTA-12314 |
| 2 | 15RH0612 | PTA-12315 |
| 3 | 15RH0613 | PTA-12316 |

Examples 1-3 were grown in field trials at 8 separate locations, 5 plants were self-pollenated under bags at each location, and harvested at maturity. Seeds from each plant were combined and analyzed for fatty acid content. Results are presented as means computed from single plant analyses below in Table II. The min and max values for each Example are also include in Table II.

TABLE II

| Example | % C18:1 (min, max) | % C18:2 | % C18:3 | % Total Sats |
|---|---|---|---|---|
| 1 | 65.59 (61.3, 69.5) | 25.84 (20.9, 29.3) | 1.65 (1.1, 2.9) | 4.32 (3.9-5.4) |
| 2 | 66.53 (59.9, 69.8) | 24.09 (21.1, 30.6) | 2.50 (2.0, 3.1) | 4.42 (4.0, 5.6) |
| 3 | 67.13 (62.2, 73.6) | 24.20 (18.0, 28.8) | 1.90 (1.4, 2.8) | 4.46 (3.8, 5.9) |

Specific examples, and particular formulations given describe exemplary embodiments, they serve the purpose of illustration only. It should be understood that various alternatives to the embodiments of the invention described may be employed in practicing the invention. It is intended that the following claims define the scope of the invention and that structures within the scope of these claims and their equivalents be covered thereby. The systems shown and described are not limited to the precise details and conditions disclosed. Method steps provided may not be limited to the order in which they are listed but may be ordered any way as to carry out the inventive process without departing from the scope of the invention.

What is claimed is:

1. A canola plant comprising seed wherein the seed comprises an oil and wherein the oil has:
   a) a total saturates content of 3.5% (wt) to 5% (wt);
   b) a linoleic acid content of 21% (wt) to 28% (wt); and
   c) a linolenic acid content of less than 3.0% (wt),
   wherein:
   the seed is non-transgenic; and
   the plant is a plant, or progeny thereof, grown from seed of American Type Culture Collection designation PTA-12314, PTA-12315, PTA-12316, or combinations thereof.

2. The plant of claim 1 wherein the total saturates content is from 4% (wt) to 5% (wt).

3. The plant of claim 1 wherein:
   a) the total saturates content is from 4% (wt) to 5% (wt);
   b) the linoleic acid content is from 24% (wt) to 28% (wt); and
   c) the linolenic acid content is from 1.5% (wt) to 3.0% (wt).

4. The plant of claim 1, wherein the oleic acid content is greater than 60% (wt).

5. The plant of claim 1, wherein the oleic acid content is 60%-70% (wt).

6. A plant or progeny thereof grown from a seed selected from the group consisting of American Type Culture Collection designation PTA-12314, PTA-12315, and PTA-12316, wherein the plant or progeny thereof comprise seed comprising an oil comprising
   a) a total saturates content of 3.5% (wt) to 5% (wt);
   b) a linoleic acid content of 21% (wt) to 28% (wt); and
   c) a linolenic acid content of less than 3.0% (wt).

7. The plant of claim 6, wherein the total saturates content is from 4% (wt) to 5% (wt).

8. The plant of claim 6, wherein the plant is non-transgenic.

9. The plant of claim 6, wherein
   a) the total saturates content is from 4% (wt) to 5% (wt);
   b) the linoleic acid content is from 24% (wt) to 28% (wt); and
   c) the linolenic acid content is from 1.5% (wt) to 3.0% (wt).

10. The plant of claim 6, wherein the oleic acid content is greater than 60% (wt).

11. The plant of claim 6, wherein the oleic acid content is 60%-70% (wt).

* * * * *